United States Patent [19]

Carrozza et al.

[11] Patent Number: 5,418,267

[45] Date of Patent: May 23, 1995

[54] PIPERIDINE COMPOUNDS CONTAINING SILANE GROUPS FOR USE AS STABILIZERS FOR ORGANIC MATERIALS

[75] Inventors: Primo Carrozza, Padova; Valerio Borzatta, Bologna, both of Italy

[73] Assignee: Ciba-Geigy Corporation, Ardsley, N.Y.

[21] Appl. No.: 234,892

[22] Filed: Apr. 28, 1994

Related U.S. Application Data

[62] Division of Ser. No. 19,520, Feb. 19, 1993, Pat. No. 5,321,066, which is a division of Ser. No. 805,429, Dec. 11, 1991, Pat. No. 5,219,905.

[30] Foreign Application Priority Data

Dec. 17, 1990 [IT] Italy ................. 22402A90

[51] Int. Cl.$^6$ ................. C07F 7/10; C07F 7/18
[52] U.S. Cl. .................. 524/99; 524/89; 524/102; 524/103; 546/14
[58] Field of Search ............. 524/99, 102, 103, 89; 525/102; 546/14

[56] References Cited

U.S. PATENT DOCUMENTS 4,177,186  8/1989  Rody et al. ............. 546/14
4,859,759  8/1989  Maycock et al. ......... 546/14

FOREIGN PATENT DOCUMENTS 0162524 11/1985  European Pat. Off. ........... 546/156
0182415  6/1986  European Pat. Off. ........... 546/14
0244026 11/1987  European Pat. Off. ........... 546/14
0263561  4/1988  European Pat. Off. ........... 546/14
0343717 11/1989  European Pat. Off. ........... 546/14
0358200  3/1990  European Pat. Off. ........... 546/14

OTHER PUBLICATIONS

Derwent Abst. 86–205176/32 & Chem Abst. 106, 5979t (1987).
Derwent Abst. 86–205177/32 & Chem. Abst. 106, 19478R (1987).
Chem. Absts. 115, 160562f (1991).

*Primary Examiner*—C. Warren Ivy
*Assistant Examiner*—Zinna N. Davis
*Attorney, Agent, or Firm*—Luther A. R. Hall

[57] ABSTRACT

The present invention relates to novel piperidine compounds of the formula (I)

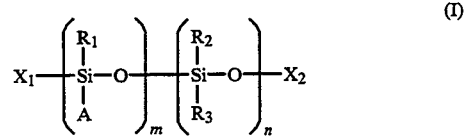

in which A is e.g. a group of the formula

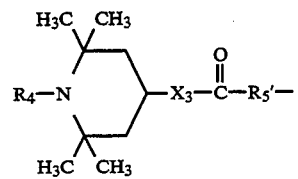

where $R_4$ is e.g. hydrogen or methyl, $X_3$ is e.g. —O— or —NH— and $R_{5'}$ is e.g. ethylene, propylene or decamethylene, $R_1$ is e.g. methyl, methoxy, ethoxy or OH, $R_2$ and $R_3$ are e.g. methyl, m+n is e.g. a number from 1 to 40, n varies e.g. from zero to 50% of the sum m+n, $X_1$ is e.g. as defined for $R_1$ or is a group $(CH_3)_3SiO$— and $X_2$ is e.g. hydrogen, methyl, ethyl, a group $(CH_3)_3Si$— or a group

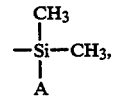

and, when m+n is a number from 3 to 10, $X_1$ and $X_2$ together also form a direct bond. The compounds of the formula (I) are effective in stabilizing an organic material against thermal, oxidative and light-induced degradation.

10 Claims, No Drawings

PIPERIDINE COMPOUNDS CONTAINING SILANE GROUPS FOR USE AS STABILIZERS FOR ORGANIC MATERIALS

This is a divisional of Ser. No. 08/019,520, filed Feb. 19, 1993, now U.S. Pat. No. 5,321,066 which is a divisional of Ser. No. 07/805,429, filed Dec. 11, 1991, now U.S. Pat. No. 5,219,905 issued Jun. 15, 1993.

The present invention relates to novel piperidine compounds containing silane groups, to their use as stabilisers for organic materials, in particular synthetic polymers, against light, heat and oxidation, and to organic materials thus stabilised.

The use of 2,2,6,6-tetramethylpiperidine derivatives containing silane groups, such as those reported in U.S. Pat. Nos. 4,177,186 and 4,859,759, EP Laid Open Prints Nos. 162 524, 182 415, 244 026, 263 561, 343 717 and 358 200 and DD Patents Nos. 234 682 and 234 683, as stabilisers for synthetic polymers is known.

The present invention relates to novel compounds of the general formula (I)

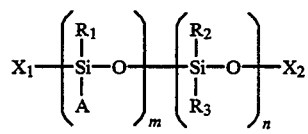

in which A is one of the groups of the formulae (IIa)–(IId)

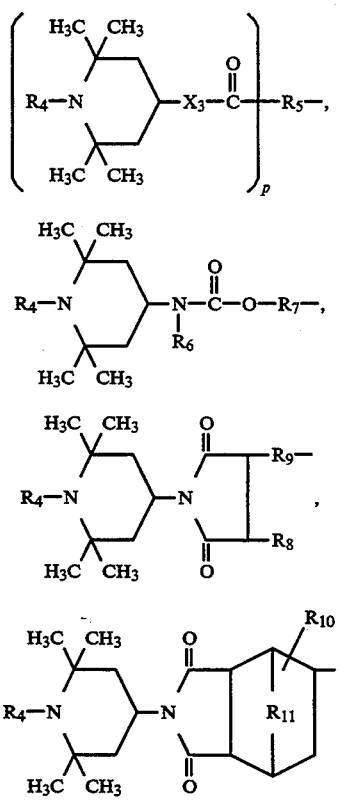

in which $R_4$ is hydrogen, $C_1$–$C_8$alkyl, O., OH, NO, $CH_2CN$, $C_1$–$C_{18}$alkoxy, $C_5$–$C_{12}$cycloalkoxy, $C_3$–$C_6$alkenyl, $C_7$–$C_9$phenylalkyl which is unsubstituted or mono-, di- or tri-substituted on the phenyl by $C_1$–$C_4$alkyl; or $_1$–$C_8$acyl, $X_3$ is —O— or >N-$R_{12}$ where $R_{12}$ is hydrogen, $C_1$–$C_{18}$alkyl, $C_5$–$C_{12}$cycloalkyl which is unsubstituted or mono-, di- or tri-substituted by $C_1$–$C_4$alkyl; $C_7$–$C_9$phenylalkyl which is unsubstituted or mono-, di- or tri-substituted on the phenyl by $C_1$–$C_4$alkyl; or tetrahydrofurfuryl, $C_2$–$C_4$alkyl substituted in the 2-, 3- or 4-position by $C_1$–$C_8$alkoxy, by di-($_1$–$C_4$alkyl)-amino or by a group of the formula (III)

where $X_4$ is a direct bond, —O—, —$CH_2$— —$CH_2CH_2$— or $H_3C$—N<, or $R_{12}$ is a group of the formula (IV),

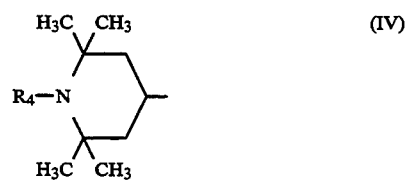

with $R_4$ as defined above, or $R_{12}$ is one of the groups of the formulae (Va)–(Vd)

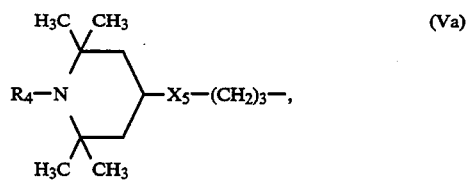

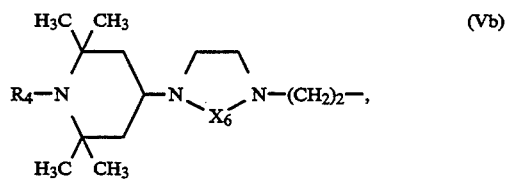

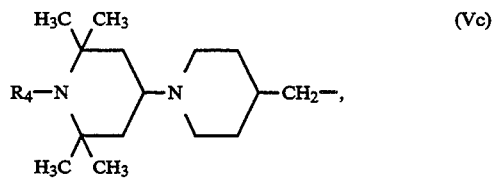

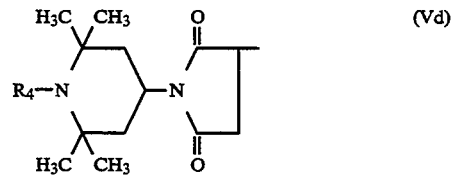

where $R_4$ is as defined above, $X_5$ is —O— or >N—$CH_3$ and $X_6$ is —$CH_2CH_2$—, —CO——COCO— or —$COCH_2CO$—, or $X_3$ is a 1,4-piperazinediyl group, p is 1, 2 or 3 and, when p is 1, $R_5$ is $C_2$–$C_{18}$alkanediyl and, when p is 2, $R_5$ is $C_2$–$C_{20}$alkanetriyl, $C_5$–$C_7$cycloalkanetriyl or $C_7$–$C_9$bicycloalkanetriyl or a group $$-\underset{\underset{(CH_2)_q}{|}}{CH}-X_7-R_{13}-$$

where $X_7$ is —O— or >N—$R_{14}$ with $R_{14}$ being $C_1$-$C_8$acyl or ($C_1$-$C_8$alkoxy)carbonyl, $R_{13}$ is $C_3$-$C_{12}$alkanediyl and q is 0 or 1, and, when p is 3, $R_5$ is $C_3$-$C_6$alkanetetrayl, $R_6$ is as defined above for $R_{12}$, $R_7$ is $C_2$-$C_{12}$alkanediyl, $R_8$ is hydrogen or methyl, $R_9$ is a direct bond, $C_1$-$C_{18}$alkanediyl or a group —$X_7$—$R_{13}$— with $X_7$ and $R_{13}$ as defined above, $R_{10}$ is hydrogen or methyl and $R_{11}$ is —$CH_2$— or —$CH_2CH_2$—, $R_1$ is $C_1$-$C_8$alkyl, phenyl, $C_1$-$C_8$alkoxy or OH, $R_2$ and $R_3$ which are identical or different are $C_1$-$C_8$alkyl or phenyl, or $R_2$ is also hydrogen, m+n is a number from 1 to 100, n varies from zero to 90% of the sum of m+n, $X_1$ is as defined for $R_1$ or is a group $(R_{15})_3SiO$— with $R_{15}$ being $C_1$-$C_8$alkyl or phenyl, $X_2$ is hydrogen, $C_1$-$C_8$alkyl, a group $(R_{15})_3Si$— or when $R_1$ and $X_1$ are $C_1$-$C_8$alkyl or phenyl, $X_2$ is additionally a group $$-\underset{\underset{A}{|}}{\overset{\overset{R_1}{|}}{Si}}-X_1,$$

and, when m+n is a number from 3 to 10, $X_1$ and $X_2$ together also form a direct bond. The compounds of the formula (I) contain structural units of the formula (Ia) or a combination of the formulae (Ia) and (Ib)

$$\left\{-\underset{\underset{A}{|}}{\overset{\overset{R_1}{|}}{Si}}-O-\right\}, \quad (Ia)$$

$$\left\{-\underset{\underset{R_3}{|}}{\overset{\overset{R_2}{|}}{Si}}-O-\right\}. \quad (Ib)$$

When the compounds of the present invention are polymers or copolymers, each of the groups A, $R_1$, $R_2$ and $R_3$ in the individual recurring structural units (Ia) and (Ib) of the formula (I) can be identical or different.

When the compounds of the present invention are copolymers, the single structural units (Ia) and (Ib) of the formula (I) can be distributed therein at random or in blocks.

Examples of alkyl having not more than 18 carbon atoms are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl.

Examples of $C_2$-$C_4$alkyl substituted by $C_1$-$C_8$alkoxy are 2-methoxyethyl, 2-ethoxyethyl, 3-methoxypropyl, 3-ethoxypropyl, 3-butoxypropyl, 3-octoxypropyl and 4-methoxybutyl. 3-Methoxypropyl and 3-ethoxypropyl are preferred.

Examples of $C_2$-$C_4$alkyl substituted by di-($C_1$-$C_4$alkyl)-amino, preferably by dimethylamino or diethylamino, are 2-dimethylaminoethyl, 2-diethylaminoethyl, 3-dimethylaminopropyl, 3-diethylaminopropyl, 3-dibutylaminopropyl and 4-diethylaminobutyl.

Examples of $C_2$-$C_4$alkyl substituted by a group of formula (III) are 2-pyrrolidinoethyl, 2-morpholinoethyl, 3-morpholinopropyl, 2-piperidinoethyl, 3-piperidinopropyl and 2-(4-methylpiperazino)-ethyl. 3-Morpholinopropyl is preferred.

Examples of alkoxy containing not more than 18 carbon atoms are methoxy, ethoxy, propoxy, isopropoxy, butoxy, isobutoxy, pentoxy, isopentoxy, hexoxy, heptoxy, octoxy, decyloxy, dodecyloxy, tetradecyloxy, hexadecyloxy and octadecyloxy.

Representative examples of $C_5$-$C_{12}$cycloalkyl $R_6$ and $R_{12}$, which is unsubstituted or mono-, di- or tri-substituted by $C_1$-$C_4$alkyl, are cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclododecyl; unsubstituted or $C_1$-$C_4$alkyl-substituted cyclohexyl is preferred.

Examples of $C_5$-$C_{12}$cycloalkoxy are cyclopentoxy, cyclohexoxy, cycloheptoxy, cyclooctoxy, cyclodecyloxy and cyclododecyloxy. Cyclopentoxy and cyclohexoxy are preferred.

Examples of $C_3$-$C_6$alkenyl are allyl, 2-methylallyl, 2-butenyl and 2-hexenyl. Allyl is preferred.

Examples of $C_7$-$C_9$phenylalkyl which is unsubstituted or mono-, di- or tri-substituted on the phenyl by $C_1$-$C_4$alkyl are benzyl, methylbenzyl, dimethylbenzyl, trimethylbenzyl, t-butylbenzyl and 2-phenylethyl. Benzyl is preferred.

Examples of $C_1$-$C_8$acyl are formyl, acetyl, propionyl, butyryl, pentanoyl, hexanoyl, heptanoyl, octanoyl, benzoyl, acryloyl and crotonyl. $C_1$-$C_8$alkanoyl, $C_3$-$C_8$alkenoyl and benzoyl are preferred. Acetyl is especially preferred.

Representative examples of $C_2$-$C_{18}$alkanediyl $R_5$, when p is 1, are ethylene, ethylidene, propylene, propylidene, trimethylene, methyltrimethylene, tetramethylene, pentamethylene, hexylene, decamethylene or groups of the formula $$CH_3(CH_2)_7-\underset{|}{CH}-(CH_2)_8-$$

or $$CH_3(CH_2)_8-\underset{|}{CH}-(CH_2)_7-.$$

Representative examples of $C_2$-$C_{12}$alkanediyl $R_7$ are ethylene, trimethylene, methyltrimethylene, tetramethylene, pentamethylene and undecamethylene.

Representative examples of $C_1$-$C_{18}$alkanediyl $R_9$ are methylene, ethylene, trimethylene or a linear or branched $C_1$-$C_{18}$alkanediyl, for example butylene, pentylene, hexylene, octylene, decylene, dodecylene, tetradecylene, hexadecylene and octadecylene.

$C_3$-$C_{12}$Alkanediyl $R_{13}$ is, for example, trimethylene, methyltrimethylene, tetramethylene, pentamethylene, hexamethylene or undecamethylene.

Representative examples of $C_2$-$C_{20}$alkanetriyl $R_5$, when p is 2, are ethanetriyl, propanetriyl, butanetriyl or a group $$-\underset{\underset{-CH_2}{|}}{CH}-R_a-$$

where $R_a$ is linear or branched $C_3$-$C_{18}$alkanediyl, for example trimethylene, butylene, pentylene, hexylene, octylene, decylene, dodecylene, tetradecylene, hexadecylene or octadecylene.

Representative examples of $C_5$-$C_7$cycloalkanetriyl or $C_7$-$C_9$bicycloalkanetriyl $R_5$ are the groups

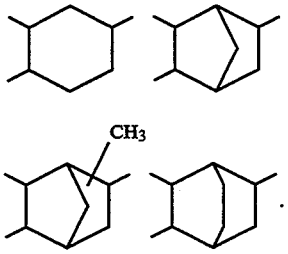

Representative examples of $C_3$-$C_6$alkanetetrayl $R_5$ are propanetetrayl, butanetetrayl and pentanetetrayl.

Representative examples of ($C_1$-$C_8$alkoxy)carbonyl are methoxycarbonyl, ethoxycarbonyl, propoxycarbonyl, isopropoxycarbonyl, butoxycarbonyl, isobutoxycarbonyl, pentoxycarbonyl, isopentoxycarbonyl, hexoxycarbonyl, heptoxycarbonyl and octoxycarbonyl.

The preferred definitions of $R_4$ are hydrogen, $C_1$-$C_4$alkyl, OH, $C_6$-$C_{12}$alkoxy, $C_5$-$C_8$cycloalkoxy, allyl, benzyl or acetyl, in particular hydrogen or methyl.

Those compounds of the formula (I) are preferred in which A is one of the groups of the formulae (IIa)–(IId) in which $X_3$ is —O— or >N—$R_{12}$ where $R_{12}$ is hydrogen, $C_1$-$C_{12}$alkyl, $C_5$-$C_8$cycloalkyl which is unsubstituted or mono-, di- or tri-substituted by $C_1$-$C_4$alkyl; benzyl which is unsubstituted or mono-, di- or tri-substituted by $C_1$-$C_4$alkyl; tetrahydrofurfuryl, $C_2$-$C_3$alkyl substituted in the 2- or 3-position by $C_1$-$C_4$alkoxy, by di-($C_1$-$C_4$alkyl)-amino or by a 1-pyrrolidyl, 1-piperidyl or 4-morpholinyl group, or $R_{12}$ is a group of the formula (IV) or one of the groups of the formulae (Va)–(Vd) in which $X_5$ is —O— or >N—$CH_3$ and $X_6$ is —$CH_2CH_2$—, —CO— or —COCO—, or $X_3$ is a 1,4-piperazinediyl group, p is 1, 2 or 3 and, when p is 1, $R_5$ is $C_2$-$C_{12}$alkanediyl and, when p is 2, $R_5$ is $C_2$-$C_{16}$alkanetriyl, $C_6$-$C_7$cycloalkanetriyl, $C_7$-$C_9$bicycloalkanetriyl or a group

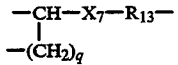

where $X_7$ is —O— or >N—$R_{14}$ with $R_{14}$ being $C_1$-$C_6$acyl or ($C_1$-$C_6$alkoxy)carbonyl, $R_{13}$ is $C_3$-$C_{11}$alkanediyl and q is zero or 1, and, when p is 3, $R_5$ is $C_3$-$C_4$alkanetetrayl, $R_6$ is as defined above for $R_{12}$, $R_7$ is $C_2$-$C_{11}$alkanediyl, $R_8$ is hydrogen or methyl, $R_9$ is a direct bond, $C_1$-$C_{12}$alkanediyl or a group —$X_7$—$R_{13}$— with $X_7$ and $R_{13}$ as defined above, $R_{10}$ is hydrogen or methyl and $R_{11}$ is —$CH_2$—, $R_1$ is $C_1$-$C_6$alkyl, phenyl, $C_1$-$C_6$alkoxy or OH, $R_2$ and $R_3$ which are identical or different are $C_1$-$C_6$alkyl or phenyl or $R_2$ is also hydrogen, m+n is a number from 1 to 80 and n varies from zero to 90% of the sum m+n, $X_1$ is as defined for $R_1$ or is a group ($R_{15}$)$_3$SiO— with $R_{15}$ being $C_1$-$C_6$ alkyl, $X_2$ is hydrogen, $C_1$-$C_6$alkyl, a group ($R_{15}$)$_3$Si— or, when $R_{15}$ and $X_1$ are $C_1$-$C_6$alkyl or phenyl, $X_2$ is additionally a group

when m+n is a number from 3 to 10, $X_1$ and $X_2$ together also form a direct bond.

Those compounds of the formula (I) are particularly preferred in which A is one of the groups of the formulae (IIa)–(IId) in which $X_3$ is —O— or >N—$R_{12}$ where $R_{12}$ is hydrogen, $C_1$-$C_{10}$alkyl, cyclohexyl which is unsubstituted or mono-, di- or trisubstituted by $C_1$-$C_4$alkyl; benzyl, tetrahydrofurfuryl, $C_2$-$C_3$alkyl substituted in the 2- or 3-position by methoxy, by ethoxy, by dimethylamino, by diethylamino or by 4-morpholinyl, or $R_{12}$ is a group of the formula (IV) or one of the groups of the formulae (Va)–(Vd) in which $X_5$ is —O— or >N—$CH_3$ and $X_6$ is —$CH_2CH_2$— or —CO—, or $X_3$ is a 1,4-piperazinediyl group, p is 1,2 or 3 and, when p is 1, $R_5$ is $C_2$-$C_{10}$alkanediyl and, when p is 2, $R_5$ is $C_2$-$C_{14}$alkanetriyl, cyclohexanetriyl or bicycloheptanetriyl or a group

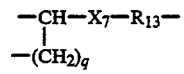

where $R_7$ is —O— or >N—$R_{14}$ with $R_{14}$ being $C_1$-$C_4$acyl or ($C_1$-$C_4$alkoxy)carbonyl, $R_{13}$ is trimethylene and q is zero or 1, and, when p is 3, $R_5$ is propanetetrayl, $R_6$ is as defined above for $R_{12}$, $R_7$ is $C_2$-$C_{11}$alkanediyl, $R_8$ is hydrogen or methyl, $R_9$ is a direct bond, $C_1$-$C_{12}$alkanediyl or a group —$X_7$—$R_{13}$— with $X_7$ and $R_{13}$ being as defined above, $R_{10}$ is hydrogen or methyl and $R_{11}$ is —$CH_2$—, $R_1$ is $C_1$-$C_4$alkyl, phenyl, $C_1$-$C_4$alkoxy or OH, $R_2$ and $R_3$ which are identical or different are $C_1$-$C_4$alkyl or phenyl, or $R_2$ is also hydrogen, m+n is a number from 1 to 60 and n varies from zero to 90% of the sum m+n, $X_1$ is as defined for $R_1$ or is a group ($R_{15}$)$_3$SiO— with $R_{15}$ being $C_1$-$C_4$alkyl, $X_2$ is hydrogen, $C_1$-$C_4$alkyl, a group ($R_{15}$)$_3$Si— or, when $R_1$ and $X_1$ are $C_1$-$C_4$alkyl or phenyl, $X_2$ is additionally a group

and, when m+n is a number from 3 to 10, $X_1$ and $X_2$ together also form a direct bond.

Those compounds of the formula (I) are of special interest in which A is a group of the formula (IIa) or (IIb) in which $X_3$ is —O— or >N—$R_{12}$ where $R_{12}$ is hydrogen, $C_1$-$C_8$alkyl, cyclohexyl, benzyl, tetrahydrofurfuryl, a group of the formula (IV) or a group of the formula (Va) or (Vb) in which $X_5$ is —O— or >N—$CH_3$ and $X_6$ is $CH_2CH_2$— or $X_3$ is a 1,4-piperazinediyl group, p is 1 or 2 and, when p is 1, $R_5$ is $C_2$-$C_{10}$alkanediyl and, when p is 2, $R_5$ is $C_2$-$C_{14}$alkanetriyl, $R_6$ is as defined above for $R_{12}$, $R_7$ is $C_2$-$C_4$alkanediyl, $R_1$ is $C_1$-$C_3$alkyl, $C_1$-$C_3$alkoxy or OH, $R_2$ and $R_3$ are $C_1$-$C_3$alkyl or $R_2$ is also hydrogen, m+n is a number from 1 to 50 and n varies from zero to 75% of the sum m+n, $X_1$ is as defined for $R_1$ or is a group ($R_{15}$)$_3$SiO— with $R_{15}$ being $C_1$-$C_3$alkyl, $X_2$ is hydrogen, $C_1$-$C_3$alkyl, a group $(R_{15})_3Si-$ or, when $R_1$ and $X_2$ are $C_1$-$C_3$alkyl, $X_1$ is additionally a group

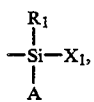

when m+n is a number from 3 to 10, $X_1$ and $X_2$ together also form a direct bond.

Those compounds of the formula (I) are of particular interest in which A is a group of the formula (IIa) or (IIb) in which $R_4$ is hydrogen or methyl, $X_3$ is —O— or —NH—, p is 1 or 2, and when p is 1, $R_5$ is $C_2$-$C_{10}$alkanediyl and, when p is 2, $R_5$ is $C_2$-$C_{14}$alkanetriyl, $R_6$ is hydrogen, $C_1$-$C_4$alkyl, 2,2,6,6-tetramethyl-4-piperidyl or 1,2,2,6,6-pentamethyl-4piperidyl and $R_7$ is trimethylene, $R_1$ is methyl, methoxy, ethoxy or OH, $R_2$ and $R_3$ are methyl, m+n is a number from 1 to 40, n varies from zero to 50% of the sum m+n, $X_1$ is as defined for $R_1$ or is a group $(CH_3)_3SiO-$ and $X_2$ is hydrogen, methyl, ethyl, a group $(CH_3)_3Si-$ or, when $R_1$ and $X_2$ are methyl, $X_2$ is additionally a group

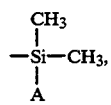

and, when m+n is a number from 3 to 10, $X_1$ and $X_2$ together also form a direct bond.

In the compounds of the formula (I) A is preferably a group of the formula

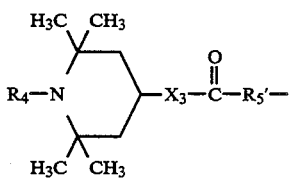

where $R_4$ is hydrogen or methyl, $X_3$ is —O— or —NH— and $R_5'$ is ethylene, propylene or decamethylene.

A further preferred meaning of A is the group of the formula

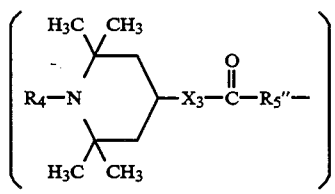

where $R_4$ is hydrogen or methyl, $X_3$ is —O— or —NH— and $R_5''$ is a group —$CH_2$—CH< or >CH—$(CH_2)_3$—.

An especially preferred meaning of A is the group of the formula

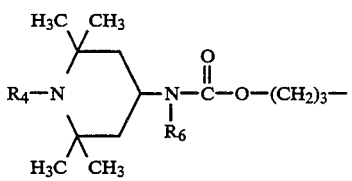

where $R_4$ is hydrogen or methyl and $R_6$ is hydrogen or $C_1$-$C_4$alkyl.

Those compounds of the formula (I) are also of particular interest, in which A is a group of the formulae (IIa), (IIb) or (IIc) in which $R_4$ is hydrogen or methyl, $X_3$ is —O— or >N—$R_{12}$ where $R_{12}$ is hydrogen or $C_1$-$C_4$alkyl, p is 1 or 2 and, when p is 1, $R_5$ is $C_2$-$C_{10}$-alkanediyl and, when p is 2, $R_5$ is $C_2$-$C_{14}$alkanetriyl, $R_6$ is as defined above for $R_{12}$, $R_7$ is $C_2$-$C_4$alkanediyl, $R_8$ is hydrogen or methyl, $R_9$ is $C_1$-$C_{12}$alkanediyl, $R_1$ is $C_1$-$C_3$alkyl, $C_1$-$C_3$alkoxy or OH, $R_2$ and $R_3$ are $C_1$-$C_3$alkyl or $R_2$ is also hydrogen, m+n is a number from 1 to 50 and n varies from zero to 75% of the sum m+n, $X_1$ is as defined for $R_1$ or is a group $(R_{15})_3SiO-$ with $R_{15}$ being $C_1$-$C_3$alkyl, $X_2$ is hydrogen, $C_1$-$C_3$alkyl, a group $(R_{15})_3Si-$ or, when $R_1$ and $X_2$ are $C_1$-$C_3$alkyl, $X_1$ is additionally a group

and, when m+n is a number from 3 to 10, $X_1$ and $X_2$ together also form a direct bond.

The compounds of the present invention can be prepared by diverse processes known per se.

Process 1—When m is 1, n is zero, $R_1$ is $C_1$-$C_8$alkyl or $C_1$-$C_8$alkoxy, $X_1$ is $C_1$-$C_8$alkyl, $C_1$-$C_8$or a group $(R_{15})_3SiO-$ and $X_2$ is $C_1$-$C_8$alkyl, a group $(R_{15})_3Si-$ or a group

with $R_1$ and $X_1$ being $C_1$-$C_8$alkyl or phenyl, the compounds of the formula (I) can be prepared, for example, in accordance with scheme 1 by reacting an alkene, capable of forming a group A as defined above, with a silane of the formula (VI)

Scheme 1

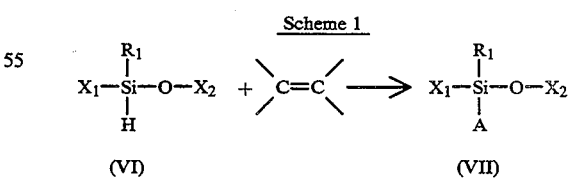

The hydrosilylation reaction (see Speier, J.A.C.S. 79, 974, (1957)) is in particular carried out in the presence of a catalytic quantity of Pd, Pt, Rh or derivatives thereof, preferably of Pt and Rh complexes, in particular $H_2PtCl_6$ and the $PtCl_2(Ph-CH=CH_2)_2$ complex, operating in the absence of solvent or in an inert solvent, for example tetrahydrofuran, dioxane, hexane, heptane, cyclohexane, toluene or xylene, at temperatures between 60° C. and 150° C., preferably between 80° C. and 130° C.

Process 2—By total or partial hydrolysis of the compounds of the formula (VII) containing at least one alkoxy group bound to a silicon atom, the corresponding silanol compounds can be prepared, from which the corresponding compounds of the formula (I) with m being at least 2 and n being zero can be obtained by condensation reactions.

The hydrolysis and condensation reactions are preferably carried out simultaneously, by treating the compounds of the formula (VII) containing alkoxysilane groups with water in a quantity of at least 0.5 mol per alkoxy group in the presence of a catalyst, preferably an inorganic acid, for example HCl $H_2SO_4$ or $H_3PO_4$, or an organic acid, for example formic or acetic acid, operating at temperatures between $-10°$ C. and 50° C., preferably between 0° C. and 30° C.

When the hydrolysis/condensation reaction is carried out in the presence of appropriate quantities of a disiloxane $[(R_{15})_3Si]_2O$, the compounds of the formula (I) with m being at least 2 and n being zero, in which $X_1$ is a group $(R_{15})_3SiO—$ and $X_2$ is a group $(R_{15})_3Si—$, can be obtained.

The hydrolysis/condensation reactions are preferably carried out in water or in the same solvent as that used for the preparation of the compounds of the formula (VII).

Process 3—When m is at least 2 and n is other than zero, the compounds of the formula (I) can be prepared by hydrolysis/condensation of mixtures in the appropriate ratios of compounds of the formula (VII) and of compounds of the formula (VIII) or (IX)

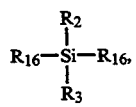

(VIII)

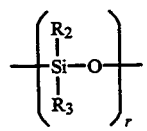

(IX)

in which $R_2$ and $R_3$ are as defined above, $R_{16}$ is $C_1$-$C_8$alkoxy and r is 3 or 4, if desired in the presence of appropriate quantifies of the disiloxane $[(R15)_3Si]20$ as chain terminator, operating under the conditions indicated in process 2.

Process 4—Compounds of the formula (I) with m being at least 2 and n being equal to or other than zero, can also be prepared by reacting a compound of the formula (X)

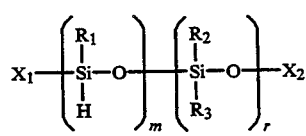

(X)

where $X_1$, $X_2$, $R_1$, $R_2$ and $R_3$ are as defined above, excluding $R_2$ defined as hydrogen, with appropriate quantities of an alkene capable of forming a group A as defined above, operating as stated under process 1.

In this reaction, it is possible to have a total or partial substitution of the hydrogen atoms bound to the silicon atoms, but not less than 30% of theory.

As mentioned at the outset, the compounds of the formula (I) are highly effective in improving the light stability, heat stability and oxidation stability of organic materials, in particular synthetic polymers and copolymers.

Examples of such organic materials which can be stabilised are:

1. Polymers of monoolefins and diolefins, for example polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefines and diolefines with each other or with other vinyl monomers, such as, for example, ethylene/propylene, linear low density polyethylene (LLDPE) and its mixtures with low density polyethylene (LDPE), propylene/butene-1, ethylene/hexene, ethylene/ethylpentene, ethylene/heptene, ethylene/octene, propylene/isobutylene, ethylene/butene-1, propyl/butadiene, isobutylene/isoprene, ethylene/alkyl acrylates, ethylene/alkyl methacrylates, ethylene/vinyl acetate copolymers and their copolymers with carbon monoxide or ethylene/acrylic acid copolymers and their salts (ionomers) and terpolymers of ethylene with propylene and a diene, such as hexadiene, dicyclopentadiene or ethylidene-norbornene; as well as mixtures of such copolymers and their mixtures with polymers mentioned in 1) above, for example polypropylene/ethylene-propylene-copolymers, LDPE-/ethylene-vinyl acetate copolymers (EVA), LDPE-/ethylene-acrylic acid copolymers (EAA), LLDPE/EVA, LLDPE/EAA and statistical or alternating polyalkylene/carbon monoxide-copolymers as well as their mixtures with other polymers, for example polyamide.

3a. Hydrocarbon resins (for example $C_5$-$C_9$) and hydrogenated modifications thereof (for example tackyfiers) and mixtures of polyalkylenes and starch.

4. Polystyrene, poly-(p-methylstyrene), poly-($\alpha$-methylstyrene).

5. Copolymers of styrene or $\alpha$-methylstyrene with dienes or acrylic derivatives, such as, for example, styrene/butadiene, styrene/acrylonitrile, styrene/alkyl methacrylate, styrene/maleic anhydride, styrene/butadiene/alkyl acrylate, styrene/butadiene/alkyl methacrylate styrene/acrylonitrile/methyl acrylate; mixtures of high impact strength from styrene copolymers and another polymer, such as, for example, from a polyacrylate, a diene polymer or an ethylene/propylene/diene terpolymer, and block copolymers of styrene, such as, for example, styrene/butadiene/styrene, styrene/isoprene/styrene, styrene/ethylene/butylene/styrene or styrene/ethylene/propylene/styrene.

6. Graft copolymers of styrene or $\alpha$-methylstyrene such as, for example, styrene on polybutadiene, styrene on polybutadiene-styrene or polybutadiene-acrylonitrile; styrene and acrylonitrile (or methacrylonitrile)

on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, copolymers of ethylene and chlorinated ethylene, epichlorohydrin homo- and copolymers, polymers from halogen-containing vinyl compounds, as for example, poly-vinylchloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.

8. Polymers which are derived from α, β-unsaturated acids and derivatives thereof, such as polyacrylates and polymethacrylates, with butyl acrylate impact resistant modified polymethyl methacrylate, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl butyral, polyallyl phthalate or polyallylmelamine; as well as their copolymers with olefins mentioned in 1) above.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as a comonomer, polyacetals modified with thermoplastic polyurethanes, acrylates or MBS.

13. Polyphenylene oxides and sulfides, and mixtures of polyphenylene oxides with polystyrene or polyamides.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, 6/10, 6/9, 6/12, 4/6, 12/12 polyamide 11, polyamide 12, aromatic polyamides obtained by condensation of m-xylene diamine and adipic acid; polyamides prepared from hexamethylenediamine and isophthalic or/and terephthalic acid and optionally an elastomer as modifier, for example poly-2,4,4,-trimethylhexamethylene terephthalamide or poly-m-phenylene isophthalamide. Further copolymers of the aforementioned polyamides with polyolefins, olefin copolymers, ionomers or chemically bonded or grafted elastomers; or with polyethers, such as for instance, with polyethylene glycols, polypropylene glycols or polytetramethylene glycols. Polyamides or copolyamides modified with EPDM or ABS. Polyamides condensed during processing (RIM-polyamide systems).

16. Polyureas, polyimides and polyamide-imides.

17. Polyesters which am derived from dicarboxylic acids and diols and [ch] or from hydroxycarboxylic acids or the corresponding lactones, such as polyethylene terephthalate, polybutylene terephthalate, poly-1,4-dimethylolcyclohexane terephthalate, poly-[2,2,-(4-hydroxyphenyl)-propane] terephthalate and polyhydroxybenzoates as well as block-copolyetheresters derived from polyethers having hydroxyl end groups.

18. Polycarbonates and polyester-carbonates.

19. Polysulfones, polyether-sulfones and polyether-ketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low inflammability.

23. Thermosetting acrylic resins, derived from substituted acrylic esters, such as epoxy-acrylates, urethane-acrylates or polyester-acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatine and derivatives thereof which are chemically modified in a polymer-homologous manner, such as cellulose acetates, cellulose propionates and cellulose butyrates, or the cellulose ethers, such as methylcellulose; rosins and their derivatives.

27. Mixtures of polymers as mentioned above, for example PP/EPDM, Polyamide 6/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6.6 and copolymers, PA/HDPE, PA/PP, PA/PPE.

28. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellithates) and also mixtures of synthetic esters with mineral oils in any weight ratios, which materials may be used as plasticizer for polymers or as textile spinning oils, as well as aqueous emulsions of such materials.

29. Aqueous emulsions of natural or synthetic rubber, e.g. natural latex or latices of carboxylated styrene/-butadiene copolymers.

The compounds of the formula (I) are particularly suitable for improving the light stability, heat stability and oxidation stability of polyolefins, especially polyethylene and polypropylene.

The compounds of the formula (I) can be used in mixtures with organic materials in various proportions depending on the nature of the material to be stabilised, on the end use and on the presence of other additives.

In general, it is appropriate to use, for example, 0.01 to 5 % by weight of the compounds of the formula (I), relative to the weight of the material to be stabilised, preferably between 0.05 and 1%.

In general, the compounds of the formula (I) can be added to the polymeric materials before, during or after the polymerisation or crosslinking of the said materials.

The compounds of the formula (I) can be incorporated in the polymeric materials in the pure form or encapsulated in waxes, oils or polymers.

The compounds of the formula (I) can be incorporated in the polymeric materials by various processes, such as dry mixing in the form of powder, or wet mixing in the form of solutions or suspensions or also in the form of a masterbatch; in such operations, the polymer can be used in the form of powder, granules, solutions, suspensions or in the form of latices.

The materials stabilised with the products of the formula (I) can be used for the production of mouldings, films, tapes, monofilaments, fibres, surface coatings and the like.

If desired, other conventional additives for synthetic polymers, such as antioxidants, UV absorbers, nickel stabilisers, pigments, fillers, plasticisers, antistatic agents, flameproofing agents, lubricants, corrosion inhibitors and metal deactivators, can be added to the mixtures of the compounds of the formula (I) with the organic materials.

Particular examples of additives which can be used in mixture with the compounds of the formula (I) are:

1. Antioxidants 1.1. Alkylated monophenols, for example 2,6-di-tert-butyl-4-methyl-phenol, 2-tert-butyl-4,6-dimethylphenol, 2,6-di-tert-butyl-4-ethylphenol, 2,6-di-tert-butyl-4-n-butyl-pheny, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4-dimethyl-6-(1'-methyl-undec-1'-yl)-phenol, 2,4-dimethyl-6-(1'-methylheptadec-1'-yl)-phenol, 2,4-dimethyl-6-(1'-methyl-tridec-1'-yl)phenol and mixtures thereof.

1.2. Alkylthiomethylphenols, for example 2,4-dioctyl-thiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxy-phenol, 2,5-di-tert-butylhydroquinone, 2,5-di-tert-amylhydroquinone, 2,6-diphenyl-4-octadecyloxyphenol, 2,6-di-tert-butyl-hydroquinone, 2,5-di-tert-butyl-4-hydroxyanisole, 3,5-di-tert-butyl-4-hydroxyanisole, 3,5-di-tert-butyl-4-hydroxyphenyl-stearate, bis-(3,5-di-tert-butyl-4-hydroxyphenyl)adipate.

1.4. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thio-bis-(3,6-di-sec-amylphenol), 4,4'-bis-(2,6-dimethyl-4-hydroxyphenyl.

1.5. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl-4-nonylphenol], 4,4'-methylenebis(2,6-di-tert-butylphenol, 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)3-n-dodecylmercaptobutane, ethylene glycol bis [3,3-bis-3'-tert-butyl-4'-hydroxyphenyl)butyrate],3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butan, 2,2-bis-(3,5-di-tert.-butyl-4-hydroxyphenyl)-propan, 2,2-bis-(5-tert.-butyl-4-hydroxy-2-methylphenyl)-4-n-dodecylmercapto-butan, 1,1,5,5-tetra-(5-tert.-butyl-4-hydroxy-2-methylphenyl)-pentan.

1.6. O-, N- and S-benzyl compounds, for example 3,5,3',5'-tetra-tert.-butyl-4,4'-dihydroxydibenzylether, octadecyl-4-hydroxy-3,5-dimethylbenzylmercaptoacetate, tris-(3,5-di-tert.-butyl-4-hydroxybenzyl)-amine, bis-(4-tert.-butyl-3-hydroxy-2,6-dimethylbenzyl)-dithioterephthalate, bis-(3,5-di-tert.-butyl-4-hydroxybenzyl)-sulfide, isooctyl-3,5-di-tert.-butyl-4-hydroxybenzyl-mercaptoacetate.

1.7. Hydroxybenzylated Malonates, for example dioctadecyl-2,2-bis-(3,5-di-tert.-butyl-2-hydroxybenzyl)-malonate, di-octadecyl-2-(3-tert.-butyl-4-hydroxy-5-methylbenzyl)-malonate, di-dodecylmercaptoethyl-2,2-bis-(3,5-di-tert.-butyl-4-hydroxybenzyl)-malonate, Di-[4-( 1,1,3,3-tetramethylbutyl)-phenyl]-2,2-bis-(3,5-di-tert.-butyl-4-hydroxybenzyl)-malonate.

1.8. Hydroxybenzyl-Aromatics, for example 1,3,5-tris-(3,5-tert.-butyl-4-hydroxybenzyl)-2,4,6-trimethylbenzene, 1,4-bis-(3,5-tert.-butyl-4-hydroxybenzyl)-2,3,5,6-tetramethylbenzene, 2,4,6-tris-(3,5-di-tert.-butyl-4-hydroxybenzyl)-phenol.

1.9. Triazine Compounds., for example 2,4-bis-octylmercapto-6-(3,5-di-tert.-butyl-4-hydroxyanilino)-1,3,5-triazine, 2-octylmercapto-4,6-bis-(3,5-di-tert.-butyl-4-hydroxyanilino)- 1,3,5-triazine, 2-octylmercapto-4,6-bis-(3,5-di-tert.-butyl-4-hydroxyphenoxy)-1,3,5-triazine, 2,4,6-tris-(3,5-di-tert.-butyl-4-hydroxyphenoxy)-1,2,3-triazine, 1,3,5-tris-(3,5-di-tert.-butyl-4-hydroxybenzyl)-isocyanurate, 1,3,5-tris-(4-tert.-butyl-3-hydroxy-2,6dimethylbenzyl)-isocyanurate, 2,4,6-tris-(3,5-di tert.-butyl-4-hydroxyphenylethyl-1,3,5-triazine, 1,3,5-tris-(3,5-di-tert.butyl-4-hydroxyphenylethyl)-1,3,5-triazine, 1,3,5-tris-(3,5-dicyclohexyl-4-hydroxybenzyl)-isocyanurate.

1.10. Benzylphosphonates, for example dimethyl-2,5-di-tert.-butyl-4-hydroxybenzylphosphonate, diethyl-3,5-di-tert.-butyl-4-hydroxybenzylphosphonate, dioctadecyl-3,5-di-tert.-butyl-4-hydroxybenzylphosphonate, dioctadecyl-5-tert.-butyl-4-hydroxy-3-methylbenzylphosphonate, Ca-salt of the 3,5-di-tert.-butyl-4-hydroxybenzyl-phosphonic acid monoethylester.

1.11. Acylaminophenols, for example lauric acid 4-hydroxyanilide, stearic acid 4-hydroxyanilide, octyl N-(3,5-di-tert-butyl-4-hydroxyphenyl)-carbamate.

1.12. Esters of β-(3,5-di-tert-butyl-4-hydroxyphenyl)-propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalic acid diamide, 3-thiaundecanol, 3-thiapentadecanol, trimethylhexanediol, trimethylolpropane, 4-hydroxymethyl-1-phospha-2,6,7-trioxabicyclo[2.2.2]-octane.

1.13. Esters of β-(5-tert-butyl-4-hydroxy-3-methylphenyl)propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalic acid diamide, 3-thiaundecanol, 3-thiapentadecanol, trimethylhexanediol, trimethylolpropane, 4-hydroxymethyl-1-phospha-2,6,7-trioxabicyclo[2.2.2]-octane.

1.14 Esters of β-(3,5-dicyclohexyl-4-hydroxyphenyl)-propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalic acid diamide, 3-thiaundecanol, 3-thiapentadecanol, trimethylhexanediol, trimethylolpropane, 4-hydroxymethyl-1-phospha-2,6,7-trioxabicyclo[2.2.2]-octane.

1.15 Esters of 3,5-di-tert.-butyl-4-hydroxyphenyl acetic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalic acid diamide, 3-thiaundecanol, 3-thiapentadecanol, trimethylhexanediol, trimethylolpropane, 4-hydroxymethyl- 1 -phospha-2,6,7-trioxabicyclo[2.2.2]-octane.

1.16. Amides of β-(3,5-di-tert-butyl-4-hydroxyphenyl)-propionic acid e.g. N,N'-bis(3,5-di-tert-butyl-4-hydroxyphenylpropionyl)hexamethylene-diamine, N,N'-bis(3,5-di-tert-butyl-4-hydroxyphenylpropionyl)tri-methylene-diamine, N,N'-bis(3,5-di-tert-butyl-4-hydroxyphenylpropionyl)-hydrazine.

2. UV absorbers and light stabilisers 2.1.2-(2'-Hydroxyphenyl)benzotriazoles, for example the 5'-methyl, 3,5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'-octoxy, 3',5'-di-tert-amyl and 3',5'-bis-(α,α-dimethylbenzyl), mixture of 5-chloro-3-tert.-butyl-5'-(2-octyloxycarbonylethyl)- and 5-chloro-3'-tert.-butyl-5'-[2-(2-ethylhexyloxy)-carbonylethyl]-,5-chloro-3'-tert.-butyl-5'-(2-methoxycarbonylethyl)-, 3'-tert.-butyl-5'-(2-methoxycarbonylethyl)-, 3'-tert.-butyl-5'-(2-octyloxycarbonylethyl)-, 3'-tert.-butyl-5'-[2-(2-ethylhexyloxy)-carbonylethyl]-, 3'-dodecyl-5'-methyl and 3'-tert.-butyl-5'-(2-isooctyloxycarbonylethyl)-2'-hydroxyphenyl-2H-benztriazole(2), 2,2'-methylene-bis[4(1,1,3,3-tetramethylbutyl)-6-benztriazole-2-yl-phenol]; product of ester interchange of 2-(3'-tert.-butyl-5'-(2-methoxycarbonylethyl)-2'-hydroxy-phenyl]-2H-benztriazole with polyethylene glycol 300; [R—CH₂CH₂—COO(CH₂)₃]₂ with R=3'-tert.-butyl-4'-hydroxy-5'-2H-benzotriazole-2yl-phenyl.

2.2.2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tert.butylphenyl salicylate, phenyl salicylate, octylphenyl salicylate, dibenzoyl-resorcinol, bis-(4-tert.butylbenzoyl)-resorcinol, benzoylresorcinol, 2,4-di-tert.butylphenyl 3,5-di-tert.butyl-4-hydroxybenzoate, hexadecyl 3,5-di-tert.butyl-4-hydroxybenzoate, octadecyl 3,5-di-tert.-butyl-4-hydroxybenzoate, 2methyl-4,6-di-tert.-butylphenyl 3,5-di-tert.-butyl-4-hydroxybenzoate.

2.4. Acrylates, for example ethyl α-cyano-β,β-diphenylacrylate, isooctyl α-cyano-β, β-diphenylacrylate, methyl-α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzyl-phosphonic acid monoalkyl esters, e.g. of the methyl or ethyl ester, nickel complexes of ketoximes, e.g. of 2-hydroxy-4-methyl-phenyl undecyl ketoxime, nickel complexes of 1-phenyl-4-lauroyl-5-hydroxypyrazole, with or without additional ligands.

2.6. Sterically hindered amines, for example bis(2,2,6,6-tetramethyl-piperidyl) sebacate, bis-(2,2,6,6-tetramethyl-piperidyl) succinate, bis(1,2,2,6,6-pentamethylpiperidyl) sebacate, bis(1,2,2,6,6-pentamethylpiperidyl) n-butyl-3,5-di-tert-butyl-4-hydroxy-benzylmalonate, the condensation product of 1-(2-hydroxyethyl)-2,2,6,6-tetramethyl-4-hydroxypiperidine and succinic acid, the condensation product of N,N'-bis(2,2,6,6-tetramethyl-4-piperidyl)-hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl-1,2,3,4-butane-tetracarboxylate, 1,1'-(1,2-ethanediyl)bis-(3,3,5,5-tetramethylpiperazinone), 4-benzoyl-2,2,6,6-tetramethylpiperidine, 4-stearyloxy-2,2,6,6-tetramethylpiperidine, bis-(1,2,2,6,6-pentamethylpiperidyl)-2-n-butyl-2-(2-hydroxy-3,5-di-tert.-butylbenzyl)malonate, 3-n-octyl-7,7,9,9-tetramethyl-1,3,8-triazasprio[4.5]decan-2,4-dion, bis-(1-octyloxy-2,2,6,6-tetramethylpiperidyl) sebacate, bis-(1-octyloxy-2,2,6,6-tetramethylpiperidyl)succinate, product of condensation of N,N'-bis-(2,2,6,6-tetramethyl-4-piperidyl)-hexamethylene diamine and 4-morpholino-2,6-dichloro-1,3,5-triazine, product of condensation of-chloro-4,6-di-(4-n-butylamino-2,2,6,6-tetramethylpiperidyl)-1,3,5-triazine and 1,2- bis-(3-aminopropylamino)ethane, product of condensation of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dion, 3-dodecyl-1-(2,2,6,6-tetramethyl-4-piperidyl)-pyrrolidin-2,5-dion, 3-dodecyl-1-(1,2,2,6,6-pentamethyl-4-piperidyl)-pyrrolidin-2,5-dion.

2.7. Oxalic acid diamides, for example 4,4'-dioctyloxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylamino-propyl)oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxy-phenyl)-4,6-bis(2,4-dimethylphenyl)-1,3,5-triazine, 2-(2,4-dihydroxy-phenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5- triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxy-propyloxy)phenyl]-4,6-bis(2,4-dimethyl)-1,3,5triazine, 2-[2-hydroxy-4-(2-hydroxy-3-octyloxy-propyloxy)phenyl]-4,6-bis(2,4-dimethyl)-1,3,5-triazine 3. Metal deactivators, for example N,N'-diphenyloxalic acid diamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyl-oylamino-1,2,4-triazole, bis(benzylidene)-oxalodihydrazide, Oxanilide, isophthalic acid dihydrazide, sebacic acid-bis-phenyl-hydrazide, N,N'-diacetal-adipinic acid dihydrazide, N,N'-bis-salicyloyl-oxalic acid dihydrazide, N,N'-bis-salicyloyl-thiopropionic acid dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diiso-decyl pentaerythritol diphosphite, bis(2,4-di-tert.-butylphenyl) pentaerythritol diphosphite, bis-(2,6-di-tert.-butyl-4-methylphenyl)-pentaerythritol diphosphite, bis-isodecyloxy-pentaerythritol diphosphite, bis-(2,4-di-tert.-butyl-6-methylphenyl)-pentaerythritol diphosphite, bis-(2,4,6-tri-tert.-butylphenyl)-pentaerythritol diphosphite, tristearyl sorbitol triphosphite, tetrakis(2,4-di-tert-butylphenyl)4,4'-biphenylene diphosphonite, 6-isooctyloxy-2,4,8,10-tetra-tert.-butyl-12H-dibenz[d,g]-1,3,2-dioxaphosphocin, 6-fluoro-2,4,8,10-tetra-tert.-butyl-12-methyl-dibenz[d,g]1,3,2-dioxaphosphocin.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecyl-mercapto)propionate.

6. Polyamide stabilisers, for example copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg behenate, Mg stearate, Na ricinoleate and K palmitate, antimony pyrocatecholate or zinc pyrocatecholate.

8. Nucleating agents for example, 4-tert.butyl-benzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxydes, carbon black, graphite.

10. Other additives, for example, plasticisers, lubricants, emulsifiers, pigments, optical brighteners, flame-proofing agents, antistatic agents and blowing agents.

The compounds of the formula (I) can also be used as stabilisers, especially as light stabilisers, for almost all materials known in the an of photographic reproduction and other reproduction techniques as e.g. described in Research Disclosure 1990, 31429 (page 474 to 480).

Several examples of the preparation and use of the compounds of the formula (I) are reported for a more detailed illustration of the present invention; these examples are given solely for illustrative purposes and do not imply any restriction.

The compounds of Examples 1, 4, 11, 12 and 13 are of particular interest.

EXAMPLE 1

Preparation of the compound of the formula $$\left[ \begin{array}{c} H_3C \quad CH_3 \\ HN \underset{H_3C \quad CH_3}{\bigcirc} -OOC \end{array} \right]_2 CH-(CH_2)_3-\underset{CH_3}{\overset{|}{Si}}(OC_2H_5)_2$$

70 g (0.165 mol) of bis(2,2,6,6-tetramethyl-4-piperidyl) allylmalonate, 28.9 g (0.215 mol) of diethoxymethylsilane and 84 mg of $PtCl_2(PhCH=CH_2)_2$ are heated for 2 hours at 90° C. and for 2 hours at 120° C. in a closed glass reactor. After cooling to 80° C., the excess diethoxymethylsilane is removed at this temperature in vacuo (21 mbar). The residue is dissolved in 180 ml of a 2:1 (by volume) tetrahydrofuran/n-hexane mixture, and the solution is filtered over silica gel. After evaporation of the solvent mixture in vacuo, a light-coloured viscous oil is obtained.

Analysis for $C_{29}H_{56}N_2O_6Si$ Calculated: C=62.55%; H=10.14%; N=5.03% Found: C=62.24%; H=10.04%; N=5.08%

EXAMPLE 2

Following the procedure described in Example 1, using 115 g (0.255 mol) of bis(1,2,2,6,6-pentamethyl-4-piperidyl) allylmalonate, 44.5 g (0.331 mol) of diethoxymethylsilane and 100 mg of $PtCl_2(PhCH=CH_2)_2$, the compound of the formula

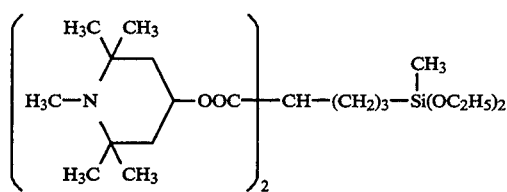

is prepared as a light-coloured viscous oil.

Analysis for $C_{31}H_{60}N_2O_6Si$ Calculated: C=63.65%; H=10.34%; N=4.79% Found: C=63.58%; H=10.29%; N=4.81%

EXAMPLE 3

Preparation of the compound of the formula

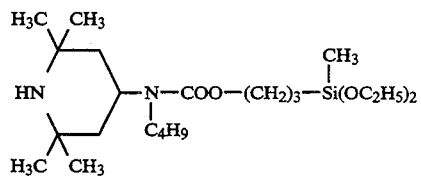

50.1 g (0.169 mol) of allyl N-butyl-N-(2,2,6,6-tetramethyl-4-piperidyl)-carbamate, 29.4 g (0.219 mol) of diethoxymethylsilane and 50 mg of $PtCl_2(Ph\text{-}CH=CH_2)_2$ are heated for 2 hours at 90° C. and for 2 hours at 120° C. in a closed glass reactor. The excess diethoxymethylsilane is removed at 80° C. in vacuo (21 mbar), and the product is separated off by distillation: boiling point 172°–174° C./0.1 mbar.

Analysis for $C_{22}H_{46}N_2O_4Si$ Calculated: C=61.35%; H=10.77%; N=6.50%; Found: C=60.85%; H=10.68%; N=6.46%

EXAMPLES 4–10

Following the procedure described in Example 3 and using the appropriate reagents, the following compounds are obtained:

| Example | Formula | Boiling point (°C./mbar) |
|---|---|---|
| 4 | H₃C−N[piperidyl(2,2,6,6-tetramethyl)]−OOC−(CH₂)₁₀−Si(CH₃)(OC₂H₅)₂ | 200–202/0.08 |
| 5 | HN[piperidyl(2,2,6,6-tetramethyl)]−OOC−CH(CH₃)−CH₂−Si(CH₃)(OC₂H₅)₂ | 283–285/1000 |
| 6 | HN[piperidyl(2,2,6,6-tetramethyl)]−NH−CO−(CH₂)₁₀−Si(CH₃)(OC₂H₅)₂ | 222–224/0.3 |
| 7 | HN[piperidyl(2,2,6,6-tetramethyl)]−OOC−(CH₂)₁₀−Si(CH₃)(OC₂H₅)₂ | 195–197/0.05 |
| 8 | H₃C−N[piperidyl(2,2,6,6-tetramethyl)]−N(C₄H₉)−COO−(CH₂)₃−Si(CH₃)(OC₂H₅)₂ | 190–192/0.1 |

-continued

| Example | Formula | Boiling point (°C./mbar) |
|---|---|---|
| 9 | 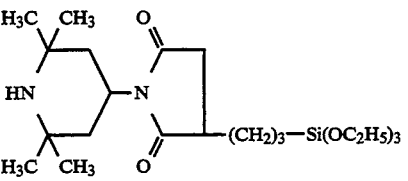 | resin (purified by chromatography) |
| 10 | 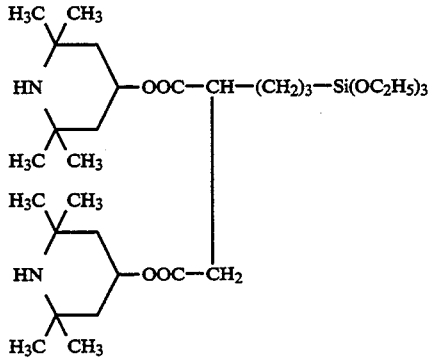 | resin (purified by chromatography) |

EXAMPLE 11

Preparation of a polysiloxane containing recurring units of the formula

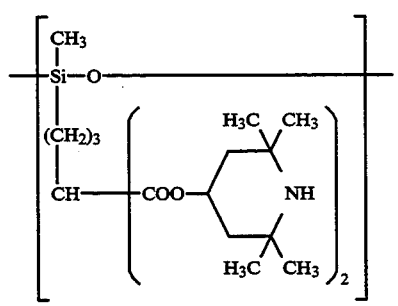

13.5 g (0.024 mol) of the product from Example 1 are dissolved in 102 ml of 1N HCl and the solution is stirred for 8 hours at ambient temperature. 100 ml of dichloromethane are added, and the mixture is neutralised with 102 ml of 1N NaOH. The organic layer is separated off, washed with water, dried over anhydrous $Na_2SO_4$ and evaporated in vacuo.

The product obtained melts at 32°–34° C. and has a molecular weight of $\overline{M}n = 1800$.

EXAMPLE 12

Following the procedure described in Example 11 and using the product from Example 2, a polysiloxane containing recurring units of the formula

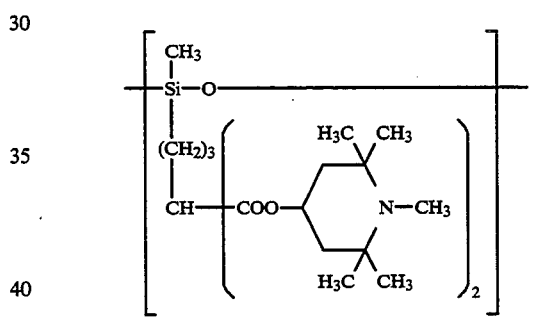

is obtained as a light-coloured dense oil of molecular weight $\overline{M}n = 2100$.

EXAMPLE 13

Following the procedure described in Example 11 and using the compound from Example 3, a polysiloxane containing recurring units of the formula

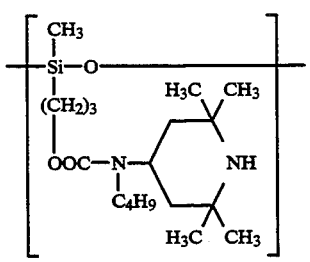

is obtained as a light-coloured dense oil of molecular weight $\overline{M}n = 1700$.

EXAMPLE 14

Following the procedure described in Example 11 and using the product from Example 4, a polysiloxane containing recurring units of the formula

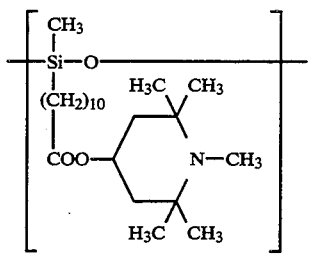

is obtained as a light-coloured dense oil of molecular weight $\overline{M}n=2000$.

EXAMPLE 15

Following the procedure described in Example 11 and using the product from Example 5, a polysiloxane containing recurring units of the formula

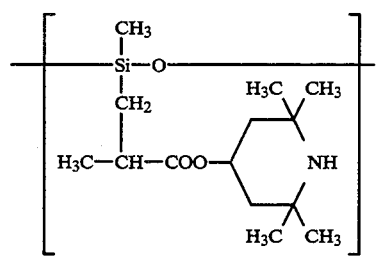

is obtained as a light-coloured dense oil of molecular weight $\overline{M}n=1000$.

EXAMPLE 16

Following the procedure described in Example 11 and using the product from Example 6, a polysiloxane containing recurring units of the formula

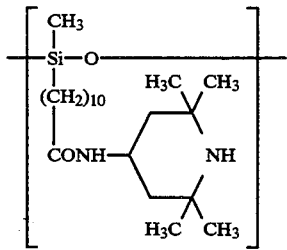

is obtained as a light-coloured dense oil of molecular weight $\overline{M}n=1900$.

EXAMPLE 17

Following the procedure described in Example 11 and using the product from Example 7, a polysiloxane containing recurring units of the formula

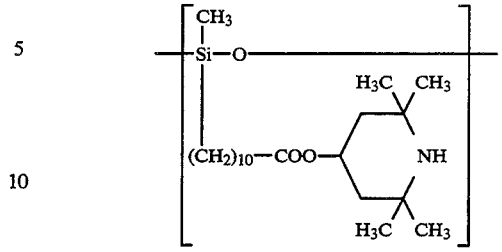

is obtained as a light-coloured dense oil of molecular weight $\overline{M}n=2600$.

EXAMPLE 18

Following the procedure described in Example 11 and using the product from Example 8, a polysiloxane containing recurring units of the formula

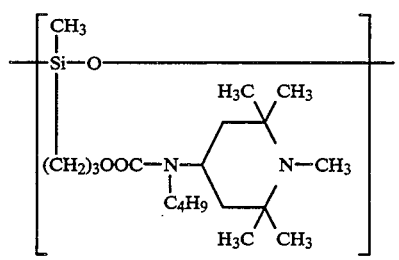

is obtained as a light-coloured dense oil of molecular weight $\overline{M}n=2000$.

EXAMPLE 19

Following the procedure described in Example 11 and using the product from Example 9, a polysiloxane containing recurring units of the formula

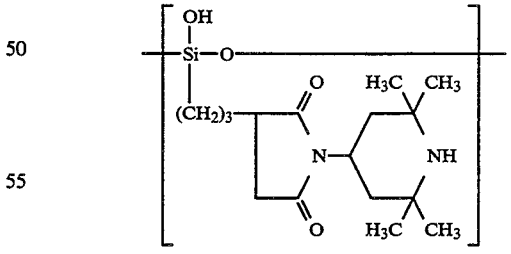

is obtained as a white wax of molecular weight $\overline{M}n=2000$.

EXAMPLE 20

Following the procedure described in Example 11 and using the product from Example 10, a polysiloxane containing recurring units of the formula

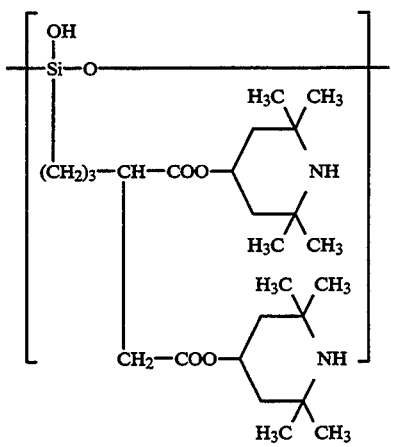

is obtained as a light-coloured dense oil of molecular weight $\overline{M}n = 1950$.

EXAMPLE 21

Preparation of a polysiloxane containing recurring units of the formulae

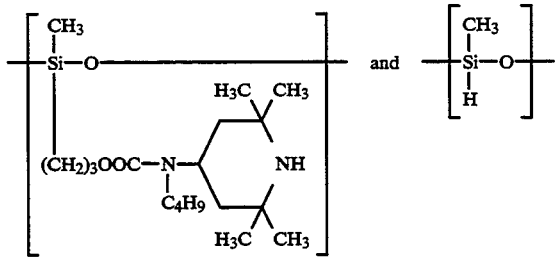

12.9 g (0.03 mol) of the product from Example 3 and 4.2 g (0.031 mol) of methyldiethoxysilane are dissolved in 100 ml of 1,2-dimethoxyethane. 2.8 ml of concentrated HCl (37% w/w) are added and the mixture is stirred 4 h at room temperature. The mixture is then neutralized with 40 ml of 1N NaOH and evaporated in vacuo (90° C./1.3 mbar).

The residue is dissolved in 100 ml of $CH_2CH_2$, washed with water until neutralization, dried over anhydrous $Na_2SO_4$ and evaporated in vacuo (80° C./1.3 mbar).

A light-coloured dense oil of $\overline{M}n = 1970$ is obtained.

In the examples, the number-average molecular weight is determined by means of a vapour pressure osmometer (®Gonotec) as described in EP-A-255,990, page 18, line 54, to page 19, line 15.

EXAMPLE 22

(light-stabilising action in polypropylene fibres):

2.5 g of each of the products indicated in Table 1, 1.0 g of a tris(2,4-di-t-butylphenyl) phosphite, 0.5 g of calcium monoethyl 3,5-di-t-butyl-4-hydroxybenzylphosphonate, 1 g of calcium stearate and 2.5 g of titanium dioxide are mixed in a slow mixer with 1000 g of polypropylene powder of melt index=12 g/10 minutes (measured at 230° C. and 2.16 kg).

The mixtures are extruded at 200°–230° C. to give polymer granules which are then converted into fibres using a pilot-type apparatus (®Leonard-Sumirago (VA), Italy) and operating under the following conditions:

Extruder temperature: 200°–230° C.
Head temperature: 255°–260° C.
Stretch ratio: 1:3.5
Count: 11 dtex per filament The fibres thus prepared are exposed, mounted on a white card, in a model 65 WR Weather-O-Meter (ASTM D 2565-85) with a black panel temperature of 63° C.

The residual tenacity is measured on samples taken after various times of exposure to light by means of a constant-speed tensometer, and the exposure time in hours ($T_{50}$) needed to halve the initial tenacity is then calculated.

Fibres prepared under the same conditions as indicated above, but without addition of the compounds of the invention, are exposed for comparison.

The results obtained are shown in Table 1:

TABLE 1

| Stabiliser | $T_{50}$ (hours) |
|---|---|
| None | 150 |
| Compound from Example 11 | 1350 |
| Compound from Example 12 | 1120 |
| Compound from Example 13 | 1330 |

EXAMPLE 23

(light-stabilising action in polypropylene tapes): 1 g of each of the compounds indicated in Table 2, 1.0 g of tris-(2,4-di-t-butylphenyl) phosphite, 0.5 g of pentaerythritol tetrakis-[3-(3,5-di-t-butyl-4-hydroxyphenyl)-propionate] and 1 g of calcium stearate are mixed in a slow mixer with 1000 g of polypropylene powder of melt index=2 g/10 minutes (measured at 230° C. and 2.16 kg).

The mixtures are extruded at 200°–230° C. to give polymer granules which are then converted into stretched tapes of 50 μm thickness and 2.5 mm width, using a pilot-type apparatus (®Leonard-Sumirago (VA), Italy) operating under the following conditions:

Extruder temperature: 210°–230° C.
Head temperature: 240°–260° C.
Stretch ratio: 1:6

The tapes thus prepared are exposed, mounted on a white card, in a model 65 WR Weather-O-Meter (ASTM D 2565-85) with a black panel temperature of 63° C. The residual tenacity is measured on samples taken after various times of exposure to light by means of a constant-speed tensometer; the exposure time (in hours) ($T_{50}$) needed to halve the initial tenacity is then calculated.

Tapes prepared under the same conditions as indicated above, but without addition of stabiliser, are exposed for comparison.

TABLE 2

| Stabiliser | $T_{50}$ (hours) |
|---|---|
| None | 300 |
| Compound of Example 11 | 3200 |
| Compound of Example 12 | 3180 |

EXAMPLE 24

(light-stabilising action in polypropylene plaques):

1 g of each of the compounds indicated in Table 3, 1.0 g of tris-(2,4-di-t-butylphenyl)phosphite, 0.5 g of pentaerythritol tetrakis-[3-(3,5-di-t-butyl-4-hydroxyphenyl)-propionate], 1 g of Blue Phthalocyanine and 1 g of calcium stearate are mixed in a slow mixer with 1000 g of polypropylene powder of melt index=2.1 g/10 minutes (measured at 230° C. and 2.16 kg).

The mixtures are extruded at 200°-220° C. to give polymer plaques of 2 mm thickness by injection-moulding at 190°-230° C.

The plaques are then exposed in a Weather-O-Meter 65 WR (ASTM G 26-77) with a black panel temperature of 63° C. until the start of superficial embrittlement (chalking).

For comparison, a polypropylene plaque prepared under the same conditions as indicated above, but without the addition of the compounds of the invention, is exposed.

Table 3 shows the exposure time (hours) required to reach the start of superficial embrittlement.

TABLE 3

| Stabiliser | Embrittlement time (hrs) |
| --- | --- |
| None | 500 |
| Compound of Example 1 | 3560 |
| Compound of Example 4 | 3980 |

What is claimed is:

1. A compound of the formula (I)

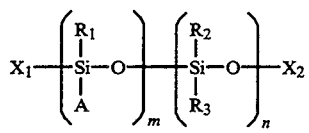

in which A is one of the groups of the formulae (IIc) and (IId)

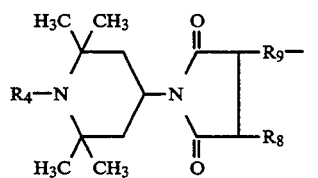

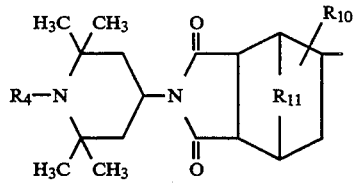

in which $R_4$ is hydrogen, $C_1-C_8$alkyl, O., OH, NO, $CH_2CN$, $C_1-C_{18}$alkoxy, $C_5-C_{12}$cycloalkoxy, $C_3-C_6$alkenyl, $C_7-C_9$phenylalkyl which is unsubstituted or mono-, di- or tri-substituted on the phenyl by $C_1-C_4$alkyl; or $C_1-C_8$acyl;

$R_8$ is hydrogen or methyl;

$R_9$ is a direct bond, $C_1-C_{18}$alkanediyl or a group —$X_7$—$R_{13}$— where $X_7$ is —O— or >N—$R_{14}$ with $R_{14}$ being $C_1-C_8$acyl or ($C_1-C_8$alkoxy)-carbonyl and $R_{13}$ is $C_3-C_{12}$alkanediyl;

$R_{10}$ is hydrogen or methyl;

$R_{11}$ is —$CH_2$— or —$CH_2CH_2$—;

$R_1$ is $C_1-C_8$alkyl, phenyl, $C_1-C_8$alkoxy or OH;

$R_2$ and $R_3$ which are identical or different are $C_1-C_8$alkyl or phenyl, or $R_2$ is also hydrogen;

m+n is a number from 1 to 100;

n varies from zero to 90% of the sum of m+n;

$X_1$ is as defined for $R_1$ or is a group $(R_{15})_3SiO$— with $R_{15}$ being $C_1-C_8$alkyl or phenyl;

$X_2$ is hydrogen, $C_1-C_8$alkyl, a group $(R_{15})_3Si$— or, when $R_1$ and $X_1$ are $C_1-C_8$alkyl or phenyl, $X_2$ is additionally a group

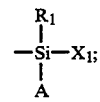

and, when m+n is a number from 3 to 10, $X_1$ and $X_2$ together also form a direct bond;

each of the groups $R_1$, $R_2$, $R_3$ and A have the same definition or different definitions in the recurring structural units contained in formula (I) and, when the compounds of the formula (I) are copolymeric, they have a random distribution or a block distribution of the individual structural units.

2. A compound of the formula (I) according to claim 1, in which A is one of the groups of the formulae (IIc) and (IId) in which $R_8$ is hydrogen or methyl;

$R_9$ is a direct bond, $C_1-C_{12}$alkanediyl or a group —$X_7$—$R_{13}$— where $X_7$ is —O— or >N—$R_{14}$ with $R_{14}$ being $C_1-C_6$acyl or ($C_1-C_6$alkoxy)-carbonyl and $R_{13}$ is $C_3-C_{11}$alkanediyl;

$R_{10}$ is hydrogen or methyl;

$R_{11}$ is —$CH_2$—;

$R_1$ is $C_1-C_6$alkyl, phenyl, $C_1-C_6$alkoxy or OH;

$R_2$ and $R_3$ which are identical or different are $C_1-C_6$alkyl or phenyl or $R_2$ is also hydrogen;

m+n is a number from 1 to 80 and n varies from zero to 90% of the sum m+n;

$X_1$ is as defined for $R_1$ or is a group $(R_{15})_3SiO$— with $R_{15}$ being $C_1-C_6$ alkyl;

$X_2$ is hydrogen, $C_1-C_6$alkyl, a group $(R_{15})_3Si$— or, when $R_1$ and $X_1$ are $C_1-C_6$alkyl or phenyl, $X_2$ is additionally a group

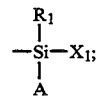

and, when m+n is a number from 3 to 10, $X_1$ and $X_2$ together also form a direct bond.

3. A compound of the formula (I) according to claim 1, in which A is one of the groups of the formulae (IIc) and (IId) in which $R_8$ is hydrogen or methyl;

$R_9$ is a direct bond, $C_1-C_{12}$alkanediyl or a group —$X_7$—$R_{13}$— where $X_7$ is —O— or >N—$R_{14}$ with $R_{14}$ being $C_1-C_4$acyl or ($C_1-C_4$alkoxy)-carbonyl and $R_{13}$ is trimethylene;

$R_{10}$ is hydrogen or methyl;

$R_{11}$ is —$CH_2$—;

$R_1$ is $C_1-C_4$alkyl, phenyl, $C_1-C_4$alkoxy or OH;

$R_2$ and $R_3$ which are identical or different are $C_1-C_4$alkyl or phenyl, or $R_2$ is also hydrogen;

m+n is a number from 1 to 60 and n varies from zero to 90% of the sum m+n;

$X_1$ is as defined for $R_1$ or is a group $(R_{15})_3SiO$— with $R_{15}$ being $C_1-C_4$alkyl;

$X_2$ is hydrogen, $C_1$-$C_4$alkyl, a group $(R_{15})_3Si$— or, when $R_1$ and $X_1$ are $C_1$-$C_4$alkyl or phenyl, $X_2$ is additionally a group

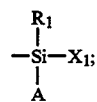

and, when m+n is a number from 3 to 10, $X_1$ and $X_2$ together also form a direct bond.

4. A compound of the formula (I) according to claim 1, in which A is a group of the formula (IIc); in which $R_4$ is hydrogen or methyl;

$R_8$ is hydrogen or methyl;

$R_9$ is $C_1$-$C_{12}$alkanediyl;

$R_1$ is $C_1$-$C_3$alkyl, $C_1$-$C_3$alkoxy or OH;

$R_2$ and $R_3$ are $C_1$-$C_3$alkyl or $R_2$ is also hydrogen;

m+n is a number from 1 to 50 and n varies from zero to 75% of the sum m+n;

$X_1$ is as defined for $R_1$ or is a group $(R_{15})_3SiO$— with $R_{15}$ being $C_1$-$C_3$alkyl;

$X_2$ is hydrogen, $C_1$-$C_3$alkyl, a group $(R_{15})_3Si$— or, when $R_1$ and $X_1$ are $C_1$-$C_3$alkyl, $X_2$ is additionally a group

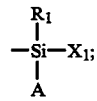

and, when m+n is a number from 3 to 10, $X_1$ and $X_2$ together also form a direct bond.

5. A compound of the formula (I) according to claim 1, in which n is zero and the repeating structural unit of the formula

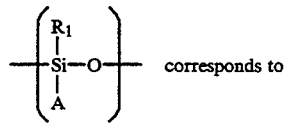 corresponds to

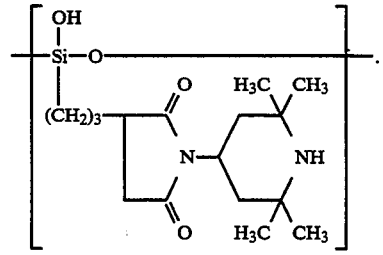

6. A compound of the formula (I) according to claim 1, in which $R_4$ is hydrogen, $C_1$-$C_4$alkyl, OH, $C_6$-$C_{12}$alkoxy, $C_5$-$C_8$cycloalkoxy, allyl, benzyl or acetyl.

7. A composition comprising a synthetic polymer susceptible to degradation induced by light, heat and oxidation and an effective stabilizing amount of a compound of the formula (I) according to claim 1.

8. A composition according to claim 7, in which the synthetic polymer is a polyolefin.

9. A composition according to claim 7, in which the synthetic polymer is polyethylene or polypropylene.

10. A method for stabilizing a synthetic polymer against degradation induced by light, heat and oxidation, which comprises incorporating into said synthetic polymer an effective stabilizing amount of a compound of the formula (I) according to claim 1.

* * * * *